United States Patent [19]

Eikenberry

[11] Patent Number: 5,155,024
[45] Date of Patent: Oct. 13, 1992

[54] BINDER COMPOSITION AND ANALYTICAL ELEMENT HAVING STABILIZED PEROXIDASE IN LAYER CONTAINING THE COMPOSITION

[75] Inventor: Jon N. Eikenberry, Rochester, N.Y.

[73] Assignee: Eastman Kodak Company, Rochester, N.Y.

[21] Appl. No.: 884,249

[22] Filed: Jul. 10, 1986

[51] Int. Cl.$^5$ .................. G01N 33/53; C12Q 1/28; C12N 9/96
[52] U.S. Cl. .................. 435/7.9; 435/7.92; 435/25; 435/28; 435/4; 435/805; 435/810; 435/288; 435/188; 422/56; 422/57; 422/60; 422/61; 436/518; 436/810
[58] Field of Search ............ 435/4, 7, 28, 805, 810, 435/291, 188; 422/56, 57, 58, 60, 61; 436/518, 808, 810, 7.92, 7.9, 25

[56] References Cited

U.S. PATENT DOCUMENTS

| | | | |
|---|---|---|---|
| Re. 28,575 | 10/1975 | Bauer | 252/408 |
| 3,050,373 | 8/1962 | Collins | 23/253 |
| 3,539,450 | 11/1970 | Deutsch | 435/188 |
| 3,860,484 | 1/1975 | O'Malley | 435/188 |
| 3,971,702 | 7/1976 | Maekawa et al. | 195/63 |
| 3,992,158 | 11/1976 | Przyblewicz et al. | 422/57 |
| 4,038,485 | 7/1977 | Johnston et al. | 23/230 B |
| 4,061,468 | 12/1977 | Lange et al. | 422/56 |
| 4,132,527 | 1/1979 | Maekawa et al. | 23/230 |
| 4,234,316 | 11/1980 | Hevey | 422/57 X |
| 4,252,896 | 2/1981 | Shaffar | 435/7 |
| 4,275,031 | 6/1981 | Fischer et al. | 422/61 X |
| 4,283,491 | 8/1981 | Dappen | 435/10 |
| 4,331,761 | 5/1982 | Dawson et al. | 435/188 |
| 4,366,243 | 12/1982 | Rupchock et al. | 435/7 |
| 4,427,632 | 1/1984 | Okaniwa et al. | 422/56 |
| 4,472,498 | 9/1984 | Masuda et al. | 435/7 |
| 4,587,102 | 5/1986 | Nagatomo et al. | 435/805 X |
| 4,670,381 | 6/1987 | Frickey et al. | 435/7 |
| 4,931,385 | 6/1990 | Block et al. | 435/7 |

FOREIGN PATENT DOCUMENTS 237327 5/1985 German Democratic Rep. .
8202601 8/1982 World Int. Prop. O. .

OTHER PUBLICATIONS

Maggio, Enzyme Immunoassay, CRC Press, Boca Raton, Florida, (1980), pp. 64–65.

Thorpe, et al., Clin. Chem. "Phenols as Enhancers of the Chemiluminescent Horseradish Peroxidase-Luminol-Hydrogen Peroxide Reaction: Application in Luminescence-Monitored Enzyme Innumoassays", 31(8), pp. 1335–1341 (1985).

Primary Examiner—Kepplinger
Assistant Examiner—Toni R. Scheiner
Attorney, Agent, or Firm—J. Lanny Tucker

[57] ABSTRACT

An analytical element has a peroxidase-labeled ligand analog distributed within a water-soluble binder composition comprising at least about 50 percent, by weight, of poly(vinyl alcohol). As a result, the peroxidase retains more of its stability prior to use. Such elements can be used to determine any of a number of immunologically reactive analytes, such as digoxin.

19 Claims, No Drawings

BINDER COMPOSITION AND ANALYTICAL ELEMENT HAVING STABILIZED PEROXIDASE IN LAYER CONTAINING THE COMPOSITION

FIELD OF THE INVENTION

The present invention relates to clinical chemistry. In particular, it relates to binder compositions, to analytical elements containing stabilized peroxidase-labeled ligand analogs and to their use in analytical methods to assay liquids, e.g. biological fluids.

BACKGROUND OF THE INVENTION

It is well known to perform a quantitative or qualitative analysis of an aqueous liquid by contacting that liquid with an analytical element containing a combination of reagents capable of yielding a detectable product in proportion to the concentration of the predetermined analyte in the liquid. As used herein, this combination of reagents is termed an interactive composition which is capable of chemical reactivity, catalytic activity, or any other form of chemical or physical interaction that can result in the ultimate production of a change in the element that is detectable with suitable procedures and equipment.

One type of particularly useful analytical elements utilizes enzymatic reactions wherein the analyte, upon contact with reagents in the element, reacts with oxygen in the presence of a suitable enzyme to produce peroxide in proportion to the concentration of the analyte. A detectable product is then produced by the reaction of the peroxide in proportion to the concentration of the analyte in the tested liquid. Such useful elements are described, for example, in U.S. Pat. No. 3,992,158 (issued Nov. 16, 1976 to Przybylowicz et al).

Unfortunately, because of the intrinsic instabilities of certain reagents and the need to dry these down in contact with other materials, the reagents contained therein may deteriorate during storage and thus deleteriously affect the accuracy and reliability of the assay. For example, exposure to air and moisture may adversely affect peroxidase which is often included in an element to catalyze the oxidation of interactive compositions by a peroxide.

Peroxidases are used for diverse purposes, including diagnostic determinations of analytes such as glucose, uric acid, cholesterol, etc. In such determinations, excess peroxidase can be added to an element to overcome the effect of enzyme deterioration during storage. However, enzyme immunoassays using a peroxidase-labeled ligand analog have become important for determining an immunologically reactive ligand such as a drug, antigen or other immunologically reactive compound. In such assays, excess peroxidase cannot be added and the adverse effect of its instability is more prominent because of the relatively low concentration of ligand to be determined.

U.S. Pat. No. 4,283,491 (issued Aug. 11, 1981 to Dappen) describes the stabilization of peroxidase in elements with a vinyl copolymer prepared from specific ethylenically unsaturated polymerizable monomers. These elements further contain reagents needed for the determination of particular analytes such as glucose and uric acid. Immunoassays are not described. The copolymer is included in the element carrier materials in an amount of from about 20 to about 50 weight percent. The remainder of the carrier materials can be one or more of a variety of binder materials, e.g. gelatin, hydrophilic celluloses, poly(vinyl alcohol), polysaccharides, etc.

It has been found, however, that peroxidase is not sufficiently stabilized by the materials described in U.S. Pat. No. 4,283,491 when peroxidase is used as a label in a ligand analog. The problem of peroxidase instability is more acute in the determination of a low level ligand in an immunoassay than in an assay of analytes such as glucose or uric acid which are generally found in test liquids in higher concentrations. Therefore, there is a need for a means to stabilize peroxidase-labeled ligand analogs in dry immunoassays.

SUMMARY OF THE INVENTION

The problems noted above are overcome with a water-soluble composition comprising a peroxidase-labeled ligand analog. The composition also comprises a water-soluble binder composition composed of at least about 50 percent, by weight, of poly(vinyl alcohol) and, optionally one or more additional binder materials.

This invention also provides an analytical element comprising an absorbent carrier material containing a peroxidase-labeled ligand analog for an immunologically reactive ligand uniformly distributed in the water-soluble binder composition described above.

In a preferred embodiment, a multilayer analytical element comprises a nonporous support having thereon, in order,
  a registration layer,
  a water-soluble layer containing a peroxidase-labeled ligand analog for an immunologically reactive ligand uniformly distributed in the water-soluble binder composition described above, and
  a porous spreading layer,
  the element further comprising an interactive composition which is capable of interacting with the ligand analog to provide a spectrophotometric signal in the presence of a substrate for peroxidase.

This invention also provides a method for the determination of an immunologically reactive ligand comprising the steps of:

A. in the presence of a receptor for an immunologically reactive ligand, contacting a sample of a liquid suspected of containing the ligand with an analytical element comprising an absorbent carrier material containing a peroxidase-labeled ligand analog for the ligand uniformly distributed in the water-soluble binder composition described above, the contacting carried out in such a manner as to form a complex of receptor and ligand analog, and B. determining the amount of the ligand as a result of the presence of complexed or uncomplexed ligand analog.

The present invention provides a means for stabilizing peroxidase-labeled ligand analogs in analytical elements. The peroxidase is stabilized sufficiently such that it can be retained in elements in low concentrations. Therefore, analytes, e.g. immunologically reactive ligands present in a test fluid in low concentrations can be rapidly and accurately determined. These advantages are achieved by putting the ligand analog in a water-soluble binder composition which includes at least about 50 percent, by weight, of poly(vinyl alcohol).

DETAILED DESCRIPTION OF THE INVENTION

The present invention relates to the determination (qualitative or quantitative measurement) of an immunologically reactive ligand in aqueous liquids. In particular, the invention can be used to assay biological fluids of either animals or humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

In the assay of this invention, the ligand to be determined and the corresponding labeled ligand analog compete for a fixed amount of common reactant. This reactant which specifically recognizes the ligand and ligand analog and reacts to form complexes with them is referred to herein as the receptor.

The method of this invention is practiced with a dry analytical element. The simplest element can be composed of an absorbent carrier material, e.g. a thin sheet of a self-supporting absorbent or bibulous material, such as filter paper or strips, which contains the binder composition described below and any other desired reagents. Alternatively, the reagents needed for an assay can be added to the element at the time of the assay. The element can be divided into two or more discrete zones with different reagents incorporated into individual zones of the carrier material. Such elements are known in the art as test strips, diagnostic elements, dip sticks, diagnostic agents and the like.

Useful absorbent carrier materials are water insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art as exemplified in U.S. Pat. Nos. 3,092,465 (issued Jun. 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued Jun. 2, 1981 to Kondo et al), and 4,312,834 (issued Jan. 26, 1982 to Vogel et al).

Preferably, the absorbent carrier material of the dry analytical element of this invention is a porous spreading zone. This zone can be self-supporting (i.e. composed of a material rigid enough to maintain its integrity), but preferably it is carried on a separate support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (fluorescence, transmission or reflectance spectroscopy). Useful supports can be prepared from paper, metal foils, films of polystyrene, polyesters [e.g. poly(ethylene terephthalate)], polycarbonates, cellulose esters (e.g. cellulose acetate), etc.

The porous spreading zone of the element can be prepared from any suitable fibrous or non-fibrous material or mixtures of either or both, as described in U.S. Pat. Nos. 4,292,272 (issued Sep. 29, 1981 to Kitajima et al), 3,992,158 (noted above) 4,258,001 (issued Mar. 24, 1981 to Pierce et al) and 4,430,436 (issued Feb. 7, 1984 to Koyama et al) and Japanese Patent Publication 57(1982)-101760 (published Jun. 24, 1982). It is desirable that the spreading zone be isotropically porous, meaning that the porosity is the same in each direction in the zone as caused by interconnected spaces or pores between particles, fibers, polymeric strands, etc.

The elements can have two or more discrete zones, either in the same layer or superimposed. At least one of which is preferably a porous spreading zone. The other zones can be reagent zones, registration zones, additional spreading zones, radiation-blocking or filter zones, subbing zones, barrier zones, etc. as those zones are known in the art. The zones are generally in fluid contact with each other, meaning that fluids, reagents and reaction products (e.g. color dyes) can pass or be transported between regions of adjacent zones. In other words, when the element is contacted with fluid, reagents become mixed and can readily move within the element. Preferably, each zone is a separately coated layer, although two or more zones can be separate regions in a single layer of the element.

The peroxidase-labeled ligand analog can be present in any zone or layer as long as it is uniformly distributed in the water-soluble binder composition described below. In a preferred embodiment, the water-soluble binder forms a distinct zone or layer in the element. More preferably, this zone or layer is adjacent to the porous spreading layer, although the two layers can be separated by a subbing or intermediate layer if desired.

The practice of this invention allows one to determine the amount of unknown ligand in a liquid sample. The ligand can be any immunologically reactive compound including, e.g. antigens, haptens, antibodies, toxins, hormones, therapeutic drugs, natural or synthetic steroids, proteins and other species which will complex specifically with a corresponding receptor. This invention is particularly useful for the determination of therapeutic drugs, e.g. digoxin.

The ligand analog useful in this invention is formed using any suitable technique known to one skilled in the art. Generally, they are prepared by covalently binding the peroxidase label to the ligand molecule which may be modified in any suitable way to achieve the binding.

The peroxidase-labeled ligand analog is uniformly distributed in a water-soluble binder composition comprising poly(vinyl alcohol) in an amount of at least about 50% and up to 100%, by weight, of the binder composition. Preferably, at least 80%, by weight, of the composition is poly(vinyl alcohol). The remainder of the composition is preferably one or more suitable synthetic or natural binder materials which are present in amounts that do not adversely affect the water-solubility of the composition. Examples of useful binder materials which can be used in combination with poly(vinyl alcohol) include gelatin, polyacrylic acid, poly(acrylamide-co-N-vinyl-2-pyrrolidone) (50:50 weight ratio) and similar copolymers, poly(N-vinyl-2-pyrrolidone), polyacrylamide, water absorbent starch-containing polymers such as those described in U.S. Pat. No. 3,935,099 (issued Jan. 27, 1976 to Weaver et al), and similar materials.

The coverage of the water-soluble binder composition in the element is at least about 0.1, and preferably from about 0.5 to about 5, $g/m^2$.

The method of this invention is carried out in the presence of a receptor for the ligand to be determined. For example, if the ligand is an antigen, the receptor is the corresponding antibody. The receptors are generally commercially available, or they can be readily prepared using known techniques and starting materials. Generally, the appropriate receptors, e.g. antibodies, are produced by inoculating a suitable animal with the ligand to produce antibodies according to an appropriate protocol, and removing the generated antibodies from the animal. The receptor can be added to the element prior to or substantially simultaneously with the test sample.

Alternatively and preferably, the receptor is immobilized within the element prior to the assay, e.g. during manufacture. For example, it can be immobilized within the absorbent carrier material. More particularly, it can be immobilized within the porous spreading zone on a carrier material, such as glass or polymeric beads or other particles, resins, fibers and the like. One useful carrier material is a microorganism, such as *Staphylococcus aureus*. Alternatively, the porous spreading zone components, e.g. beads, can serve as the carrier material for the receptor.

The method of this invention is carried out in such a manner that either complexed or uncomplexed ligand analog is measured. In a preferred embodiment, the method is carried out so that the complex formed between the receptor and labeled ligand is determined. This complex can be determined in any of a number of ways. For example, the complex can be determined by a competitive radiometric immunoassay. Alternatively and preferably, the complex is determined using an interactive composition which provides a spectrophotometric signal in the presence of a substrate for peroxidase. This composition comprises one or more reagents which can react to produce hydrogen peroxide which in turn can react with a dye precursor in the presence of peroxidase to produce a detectable dye. The interactive composition can be added to the element at the time of the assay, with or separate from the test sample. Preferably, it is incorporated in the element during manufacture. When so incorporated, the individual components of the composition can be located in one or more zones of the element. Alternatively, some of the reagents of the interactive composition can be incorporated in the element while others are added at the time of the assay. During the assay, all of the reagents are mixed and interact in the desired manner. The amounts of each component of the interactive composition to be used in the assay can be readily determined by one skilled in the art.

Useful dye precursors which can be converted into detectable dyes in the presence of hydrogen peroxide and peroxidase include various leuco dyes such as imidazole derivatives described, for example, in U.S. Pat. No. 4,089,747 (issued May 16, 1978 to Bruschi), E.P. Application 122,641 (published Oct. 24, 1984) and Japanese Patent Publications 58(1983)-045,557 58(1983)-068009 and 59(1984)-193353, and triarylmethanes described, for example, in U.S. Ser. No. 612,509, filed May 21, 1984 by Babb et al.

In a preferred embodiment, the interactive composition comprises $\alpha$-glycerol phosphate oxidase and a triarylimidazole leuco dye. This composition can be used for the determination of digoxin.

The element can have a number of other useful but optional components in one or more zones, including surfactants, buffers, hardeners, antioxidants, solvents, and others known in the art. The amounts of these materials are also within the skill of a worker in the art.

In a preferred embodiment, the element contains a phenol or aniline electron transfer agent which increases the reaction rate of peroxidase. Useful phenol and aniline electron transfer agents include 4-hydroxyacetanilide and others described in copending and commonly assigned U.S. Ser. No. 884,329 filed on even date herewith by McClune, and entitled USE OF PHENOLS AND ANILINES TO INCREASE THE RATE OF PEROXIDASE CATALYZED OXIDATION OF LEUCO DYES.

The amounts of peroxidase-labeled ligand analog and receptor used in the practice of this invention are readily determined by one skilled in the art. Generally, the ligand analog is present in the element in an amount of at least about $10^{-6}$, and preferably from about $10^{-5}$ to about $10^{-2}$, g/m$^2$. The receptor (whether incorporated in the element or added during the assay) is generally used in an amount which provides at least about $10^{-7}$, and preferably from about $10^{-6}$ to about $10^{-2}$, g/m$^2$. These amounts refers to the receptor alone and not to the receptor immobilized on a carrier. The receptor is generally immobilized on a carrier in the ratio of at least 1 part of receptor to $10^6$ parts of carrier, by weight.

A variety of different elements, depending on the method of assay, can be prepared in accordance with the present invention. Elements can be configured in a variety of forms, including elongated tapes of any desired width, sheets, slides or chips.

The method of this invention can be manual or automated. In general, ligand determination is made by taking the element from a supply roll, chip packet or other source and physically contacting it with a sample (e.g. 1-200 $\mu$l) of the liquid to be tested so that the sample, ligand analog, receptor and reagents within the element interact. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

Once the receptor has complexed with ligand and ligand analog, any suitable separation technique can be used to vertically or horizontally separate bound (or complexed) ligand analog from unbound (or uncomplexed) ligand analog.

In one embodiment, contact of the sample can be accomplished in such a manner that complexation of receptor and ligand and substantial horizontal separation of uncomplexed and complexed ligand occur during sample introduction. This contact can be carried out by hand or with a machine using a pipette or other suitable dispensing means to dispense the test sample. The sample of liquid can be applied to the element in a number of ways to effect horizontal separation. For example, a relatively large liquid sample (e.g. up to 100 $\mu$l) can be applied slowly (e.g. over at least about 5 seconds) in a continuous manner using a suitable dispensing means. Alternatively, the sample can be applied in small portions, e.g. as a series of two or more droplets (e.g. 0.1 to 1 $\mu$l) over a period of time (e.g. over at least about 5 seconds).

In another embodiment, horizontal or vertical separation can be accomplished by slowly adding a wash fluid after the liquid sample has been applied to the element. This wash causes uncomplexed materials to move away from the complexed materials.

The amount of ligand in the test sample is then determined by passing the element through suitable apparatus for detecting the receptor-ligand analog complex directly or a detectable species formed as a result of the reaction of peroxidase and substrate (e.g. change in reflection or transmission density or fluorescence). Alternatively, the uncomplexed ligand analog can be determined in a suitable manner.

In the embodiments noted above involving horizontal separation, the complexed ligand analog is measured in a finite area in the center of the contacted area. The amount of the ligand in the test sample is inversely proportional to the amount of ligand analog measured in that finite area. Generally, ligand analog measurement is carried out from about 5 to about 500 seconds after the test sample has been applied to the element.

In the following examples illustrating the practice of this invention, the materials used were obtained as follows: SURFACTANT 10 G surfactant from Olin Corporation (Stamford, Conn., U.S.A.), ZONYL FSN fluorocarbon surfactant from DuPont (Wilmington, Del., U.S.A.), and the remainder either from Eastman Kodak Company (Rochester, N.Y., U.S.A.) or prepared using standard procedures and readily available starting materials.

As used in the context of this disclosure and the claims, I.U. represents the International Unit for enzyme activity defined as one I.U. being the amount of enzyme activity required to catalyze the conversion of 1 micromole of substrate per minute under standard pH and temperature conditions for the enzyme.

EXAMPLES 1-3: COMPARATIVE EXAMPLE

These examples demonstrate the improved stability of peroxidase observed with the elements of the present invention as compared to an element outside the scope of this invention.

Three elements of this invention were prepared having a format like that shown in Example 4 below except that the antibodies on *S. aureus* were omitted in Examples 1 and 2, and Examples 2 and 3 contained a binder composition comprising poly(vinyl alcohol) (0.05-5 g/m$^2$) and gelatin (0.05-5 g/m$^2$) with 50 percent, by weight, of the binder composition being poly(vinyl alcohol).

Control elements were similarly prepared except that the binder composition was composed solely of unhardened gelatin (Control A) or poly-(acrylamide-co-N-vinyl-2-pyrrolidone) (50:50 weight ratio) (Control B).

The stability of the peroxidase in the ligand analog in each element was evaluated in the following manner.

A 10 μl sample of fluid containing 100 mmole of α-glycerol phosphate was applied to elements which had been incubated, some at 0° C. in the freezer and others at 22° C./50% relative humidity. Then the elements were incubated at 37° C. for 5 minutes and the rate of dye formation was determined in the most linear region of a plot of reflection density vs. time (usually after 1-3 minutes of incubation). The percent peroxidase activity retained was calculated by dividing the rate of dye formation observed for the element kept at 22° C./50% relative humidity by that observed for the freezer element.

The results of these tests are shown in Table I below. It is apparent from these data that the elements of the present invention have significantly improved peroxidase stability (i.e. retained peroxidase activity). Example 1 shows the most improvement since high peroxidase activity is retained for up to 3 weeks. However, Examples 2 and 3 exhibited improved keeping over the Control elements (at least 60% retained activity after 1 week keeping in an open container). Both Control elements had lost a significant amount of peroxidase activity even after the one week keeping period.

TABLE I

| Element | Peroxidase Activity Retained | | | |
|---|---|---|---|---|
| | 1 Week (Open)* | 1 Week (Closed)** | 3 Weeks (Open) | 3 Weeks (Closed) |
| Example 1 | about 100% | 97% | about 100% | 98% |
| Example 2 | 72% | 78% | 44% | 54% |
| Example 3 | 69% | 76% | 44% | 54% |
| Control A | 56% | 63% | 27% | 39% |
| Control B | 48% | 59% | 19% | 34% |

*Keeping at 22° C. and 50% relative humidity.
**Keeping at 22° C. and 50% relative humidity in an enclosed environment.

EXAMPLE 4: DETERMINATION OF DIGOXIN

This example illustrates the practice of this invention for the determination of digoxin. An element of the present invention was prepared having the following format and components:

| | | |
|---|---|---|
| Spreading Layer | Poly(vinyltoluene-co-p-t-butylstyrene-co-methacrylic acid) beads | 50-300 g/m$^2$ |
| | Poly(methylacrylate-co-2-acrylamido-2-methylpropane sulfonic acid-co-2-acetoacetoxyethyl methacrylate) adhesive | 1-10 g/m$^2$ |
| | 2-(3,5-Dimethoxy-4-hydroxy phenyl)-4,5-bis(4-dimethylaminophenyl)imidazole leuco dye | 0.01-1 g/m$^2$ |
| | *Staphylococcus aureus* coated with digoxin antibodies | 0.2-5 g/m$^2$ |
| | SURFACTANT 10G surfactant | 0.1-10 g/m$^2$ |
| | Dimedone antioxidant | 0.005-0.5 g/m$^2$ |
| Water Soluble Layer | Poly(vinyl alcohol) | 0.1-10 g/m$^2$ |
| | ZONYL FSN surfactant | 0.01-1 g/m$^2$ |
| | Potassium phosphate buffer (pH 7) | 0.01-1 g/m$^2$ |
| | Digoxin-peroxidase conjugate | $10^{-6}$-$10^{-4}$ g/m$^2$ |
| Reagent Layer | Gelatin (hardened) | 1-100 g/m$^2$ |
| | SURFACTANT 10G surfactant | 0.02-2 g/m$^2$ |
| | Potassium phosphate bufer (pH 7) | 0.05-5 g/m$^2$ |
| | α-Glycerol phosphate oxidase | 200-20,000 I.U./m$^2$ |
| | 4-Hydroxyacetanilide | 0.01-1 g/m$^2$ |
| | Poly(ethylene terephthalate) Support | |

Digoxin was determined using this element in the following manner. A series of test samples containing various amounts of the ligand, digoxin, were prepared in a buffered solution (pH 7). A 10 μl sample of each test sample was applied to the element prior to incubation for about 5 minutes at 37° C. At this time, a 10 μl sample of a wash fluid containing 100 mmole of α-glycerol phosphate was applied to the element over the area of the spreading layer contacted with the test sample to wash uncomplexed ligand analog horizontally away from complexed ligand analog, and to initiate the enzymatic reactions which produce a detectable dye. Complexed ligand analog was then determined by monitoring reflection densities at 670 nm in the center of the spotted area using a standard reflectometer. The rate of change in dye density was calculated from measurements taken between 60 and 120 seconds after application of the second fluid. The Clapper-Williams transform (*J. Optical Soc. Am.*, 43, 595, 1953) was used to determine transmission density values from reflectance density values. The concentration of digoxin in the test fluid was observed to be inversely related to the rate of dye formation.

The invention has been described in detail with particular reference to preferred embodiments thereof, but it will be understood that variations and modifications can be effected within the spirit and scope of the invention.

I claim:

1. An analytical element comprising an absorbent carrier material, said element divided into two or more discrete zones, and containing in one of said zones a peroxidase-labeled ligand analog for an immunologically reactive ligand uniformly distributed in a water-soluble binder composition comprising at least about 50 percent, by weight, of poly(vinyl alcohol).

2. The element of claim 1 further comprising an interactive composition which is capable of reacting with said ligand analog to provide a spectrophotometric signal in the presence of a substrate for peroxidase.

3. The element of claim 2 wherein said interactive composition comprises α-glycerol phosphate oxidase and a triarylimidazole leuco dye.

4. The element of claim 2 further comprising in at least one of said zones an immobilized receptor for said immunologically reactive ligand.

5. The element of claim 1 wherein said binder composition comprises an additional binder material selected from the group consisting of gelatin, polyacrylic acid, acrylamide-N-vinyl-2-pyrrolidone copolymers, polyacrylamide, poly(N-vinyl-2-pyrrolidone) and water-absorbent starch-containing polymers.

6. The element of claim 1 wherein poly(vinyl alcohol) is present in the binder composition in an amount of at least about 80 percent, by weight.

7. A multilayer analytical element comprising a nonporous support having thereon, in order,
a registration layer,
a water-soluble layer containing a peroxidase-labeled ligand analog for an immuno-logically reactive ligand uniformly distributed in a water-soluble binder composition comprising at least about 50 percent, by weight, of poly(vinyl alcohol), and
a porous spreading layer,
said element further comprising an interactive composition which is capable of interacting with said ligand analog to provide a spectrophotometric signal in the presence of a substrate for peroxidase.

8. The element of claim 7 wherein said ligand analog is peroxidase-labeled digoxin.

9. The element of claim 7 wherein said interactive composition comprises α-glycerol phosphate oxidase and a triarylimidazole leuco dye.

10. The element of claim 7 further comprising an immobilized receptor for said immunologically reactive ligand in said spreading layer.

11. The element of claim 7 wherein said ligand analog is present in a coverage of at least about $10^{-6}$ g/m$^2$.

12. A method for the determination of an immunologically reactive ligand comprising the steps of:
A. in the presence of a receptor for said ligand, contacting a sample of a liquid suspected of containing said ligand with an analytical element comprising an absorbent carrier material, said element divided into two or more discrete zones, and containing in one of said zones a peroxidase-labeled ligand analog for said ligand uniformly distributed in a water-soluble binder composition comprising at least about 50 percent, by weight, of poly(vinyl alcohol), said contacting carried out in such a manner as to form a complex of receptor and ligand analog, and
B. determining the amount of said ligand as a result of the presence of complexed or uncomplexed ligand analog.

13. The method of claim 12 wherein said receptor for said ligand is immobilized in one of said zones of said element.

14. The method of claim 12 wherein said liquid sample is contacted with said element in such a manner that said receptor-ligand analog complex is immobilized in said element and horizontal separation of uncomplexed ligand analog from immobilized complex is effected.

15. The method of claim 14 wherein said separation is accomplished with a wash step subsequent to said contacting step.

16. The method of claim 12 wherein said element comprises a nonporous support having thereon, in order,
a registration layer,
a layer containing said ligand analog uniformly distributed in a water-soluble binder composition comprising at least about 50 percent, by weight, of poly(vinyl alcohol), and
a porous spreading layer as said absorbent carrier material.

17. The method of claim 12 for the determination of digoxin in a biological fluid wherein said ligand analog is peroxidase-labeled digoxin.

18. The method of claim 12 wherein said complexed ligand analog is measured.

19. A multilayer analytical element comprising a nonporous support having thereon, in order,
a porous spreading layer, and
a water-soluble layer containing a peroxidase-labeled ligand analog for an immunologically reactive ligand uniformly distributed in a water-soluble binder composition comprising at least about 50 percent, by weight, of poly(vinyl alcohol).

* * * * *